United States Patent
Lane et al.

(10) Patent No.: US 11,312,608 B2
(45) Date of Patent: Apr. 26, 2022

(54) BEVERAGE DISPENSER WITH CUSTOMIZED NUTRITIVE LEVELS AND MULTIPLE SWEETENER SOURCES

(71) Applicant: THE COCA-COLA COMPANY, Atlanta, GA (US)

(72) Inventors: Sue Lane, Kennesaw, GA (US); Jamal Omari Wilson, Snellville, GA (US); Maxwell Pehge Friel, Duluth, GA (US); Kristin Wright, Woodstock, GA (US); Michele Carrabotta, Stamford, CT (US); Gregg Carpenter, Marietta, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 16/638,263

(22) PCT Filed: Aug. 10, 2018

(86) PCT No.: PCT/US2018/046228
§ 371 (c)(1),
(2) Date: Feb. 11, 2020

(87) PCT Pub. No.: WO2019/032969
PCT Pub. Date: Feb. 14, 2019

(65) Prior Publication Data
US 2020/0223682 A1 Jul. 16, 2020

Related U.S. Application Data

(60) Provisional application No. 62/544,196, filed on Aug. 11, 2017.

(51) Int. Cl.
*B67D 1/00* (2006.01)
*B67D 1/08* (2006.01)
*G07F 13/06* (2006.01)

(52) U.S. Cl.
CPC ......... *B67D 1/0034* (2013.01); *B67D 1/0036* (2013.01); *B67D 1/0037* (2013.01);
(Continued)

(58) Field of Classification Search
CPC .. B67D 1/0034; B67D 1/0036; B67D 1/0039; B67D 1/0888; G07F 13/065
See application file for complete search history.

(56) References Cited

U.S. PATENT DOCUMENTS 7,537,138 B2  5/2009  Bezelgues et al.
7,578,415 B2  8/2009  Ziesel et al.
(Continued)

FOREIGN PATENT DOCUMENTS

CN    101232828 A    7/2008
CN    101395086 A    3/2009
(Continued)

OTHER PUBLICATIONS

International Search Report and Written Opinion issued by the International Searching Authority (ISA/KR) in PCT Application No. PCT/US2018/046228 dated Dec. 17, 2018. 16 pages.
(Continued)

*Primary Examiner* — Jeremy Carroll
(74) *Attorney, Agent, or Firm* — Meunier Carlin & Curfman LLC

(57) ABSTRACT

A dispenser is configured to dispense food products at varying nutritive levels by dispensing a combination of sweeteners in a predetermined ratio from a plurality of sweetener sources. Using a predetermined combination of sweeteners in a predetermined ratio for a selected nutritive level for a given product ensures that the dispensed product will have a desirable flavor profile while at the same time providing increased consumer choice. A combination of caloric, mid-calorie, low calorie, and/or non-caloric sweet-
(Continued)

eners may be dispensed to produce a food product with a specified caloric level or nutritive level. For a given nutritive level selected, the product dispenser may dispense different combinations of sweeteners and/or different ratios of sweeteners for different brands or products to be dispensed. Likewise, for a given brand or product, the product dispenser may dispense different combinations of sweeteners and/or different ratios of sweeteners for different selected nutritive levels.

20 Claims, 7 Drawing Sheets

(52) U.S. Cl.
CPC ......... *B67D 1/0039* (2013.01); *B67D 1/0888* (2013.01); *G07F 13/065* (2013.01)

(56) References Cited

U.S. PATENT DOCUMENTS

| | | | |
|---|---|---|---|
| 7,757,896 B2 | 7/2010 | Carpenter et al. | |
| 7,866,509 B2 | 1/2011 | Ziesel | |
| 9,051,162 B2 | 6/2015 | Peters et al. | |
| 9,754,437 B2 | 9/2017 | Deo et al. | |
| 10,472,220 B2 | 11/2019 | Moore et al. | |
| 2007/0073557 A1 | 3/2007 | Abramson | |
| 2007/0212468 A1 | 9/2007 | White et al. | |
| 2009/0069934 A1 | 3/2009 | Newman et al. | |
| 2009/0105875 A1* | 4/2009 | Wiles ...................... | A47J 31/52 700/239 |
| 2009/0308488 A1* | 12/2009 | Bennett ................ | B67D 1/0034 141/18 |
| 2011/0049180 A1* | 3/2011 | Carpenter ............ | B67D 1/0051 222/1 |
| 2011/0123688 A1* | 5/2011 | Deo ..................... | B67D 1/0027 426/231 |
| 2012/0158173 A1* | 6/2012 | Metropulos ........... | G07F 13/065 700/236 |
| 2012/0325844 A1* | 12/2012 | Quartarone .......... | B67D 1/0031 222/1 |
| 2014/0263410 A1 | 9/2014 | Quartarone | |
| 2015/0039776 A1 | 2/2015 | Jarnagin, III | |
| 2015/0082243 A1 | 3/2015 | Taylor et al. | |
| 2015/0212661 A1* | 7/2015 | Robberechts ........... | G07F 11/70 715/810 |
| 2015/0251891 A1 | 9/2015 | Peters et al. | |
| 2016/0090288 A1* | 3/2016 | Givens, Jr. ........... | B67D 1/0888 700/283 |
| 2016/0368752 A1* | 12/2016 | Bethuy ................ | B67D 1/0047 |
| 2017/0202248 A1 | 7/2017 | White et al. | |
| 2018/0130141 A1 | 5/2018 | Carpenter et al. | |
| 2019/0308866 A1 | 10/2019 | Sawhney et al. | |

FOREIGN PATENT DOCUMENTS

| | | |
|---|---|---|
| WO | 2013/067020 A1 | 5/2013 |
| WO | 2015/022692 A2 | 2/2015 |
| WO | 2015/167846 A1 | 11/2015 |

OTHER PUBLICATIONS

International Preliminary Report on Patentability issued by the International Bureau of WIPO in PCT Application No. PCT/US2018/046228 dated Feb. 11, 2020. 12 pages.

Extended European Search Report received in connection with European Application No. 18843022.7, dated Dec. 11, 2020, 11 pages.

English Translation of First Office Action issued by the CNIPA in CN 2018800604154, dated May 5, 2021.

* cited by examiner

| Nutritive Choice | Cal/Serving (8 oz.) | Nutritive Level |
|---|---|---|
| Regular | 60-100 | $NL_1$ |
| Mid Cal | 30-60 | $NL_2$ |
| Low Cal | 10-30 | $NL_3$ |
| Diet | < 10 | $NL_4$ |

300 ⟶

206 Brand 1:     Pump Flow Rates

| Nutritive Level | $S_1$ (302) | $S_2$ (304) | $S_3$ (306) | $S_4$ (308) | ... | $S_n$ (310) |
|---|---|---|---|---|---|---|
| $NL_1$ | X |   | Z |   |   |   |
| $NL_2$ | Y | Z |   | Z |   |   |
| $NL_3$ | Z | Y |   |   |   | X |
| $NL_4$ |   | X | Z | Y |   |   |
| ⋮ |   |   |   |   |   |   |
| $NL_n$ |   |   |   | X |   | Z |

FIG. 3

206 Brand 1:

| Nutritive Level | $S_1$ (302) | $S_2$ (304) | $S_n$ (308) | $S_1'$ (402) | $S_2'$ (404) | $S_n'$ (406) | $F_1$ (408) | $F_2$ (410) | $F_n$ (412) | $A_1$ (414) | $A_n$ (416) |
|---|---|---|---|---|---|---|---|---|---|---|---|
| $NL_1$ |   |   |   |   |   |   |   |   |   |   |   |
| $NL_2$ | Y | Z |   | Z |   |   |   | X |   | Y |   |
| $NL_3$ |   |   |   |   |   |   |   |   |   |   |   |
| ⋮ |   |   |   |   |   |   |   |   |   |   |   |
| $NL_n$ |   |   |   |   |   |   |   |   |   |   |   |

FIG. 4

BEVERAGE DISPENSER WITH CUSTOMIZED NUTRITIVE LEVELS AND MULTIPLE SWEETENER SOURCES

CROSS REFERENCE TO RELATED APPLICATIONS

This application is a national stage application filed under 35 U.S.C. § 371 of PCT/US2018/046228, filed Aug. 10, 2018, which claims the benefit of U.S. Provisional Patent Application Ser. No. 62/544,196 filed Aug. 11, 2017, the disclosures of which are expressly incorporated herein by reference.

BACKGROUND

Traditional post-mix beverage dispensing systems generally mix streams of syrup, concentrate, sweetener, bonus flavors, other types of flavorings, and/or other ingredients with water or other types of diluents by flowing the syrup stream down the center of the nozzle with the water stream flowing around the outside. The syrup stream is directed downward with the water stream such that the streams mix as they fall into a consumer's cup. There is a desire for a beverage dispensing system as a whole to provide as many different types and flavors of beverages as may be possible in a footprint that may be as small as possible. Recent improvements in beverage dispensing technology have focused on the use of micro-ingredients. With micro-ingredients, the traditional beverage bases may be separated into their constituent parts at much higher dilution or reconstitution ratios.

This technology is enabled via cartridges containing the highly concentrated micro-ingredients. The micro-ingredients are mixed with sweeteners and still or sparkling water using precise metering and dosing technologies and dispensed through a nozzle that promotes in-air mixing so as to prevent carry-over. The technology includes a user input for a user to select a desired beverage, customize the beverage if desired, and pour the beverage at the dispenser. These beverages are made from precise recipes to ensure a great tasting beverage regardless of the customization.

SUMMARY

Aspects of the disclosure provide a beverage dispenser that comprises a nozzle configured to dispense a plurality of beverage ingredients to produce a finished beverage. The beverage dispenser also comprises a user interface configured to receive a selection of a beverage to be dispensed and a selection of a nutritive level for the beverage. The beverage dispenser also comprises a plurality of pumping or metering devices, each configured to supply a beverage ingredient from an ingredient source to the nozzle. The beverage dispenser also comprises a controller configured to look up a nutritive level recipe based on the nutritive level selection, the nutritive level recipe comprises an amount of one or more sweeteners to be dispensed to produce the beverage at the selected nutritive level. The controller is further configured to activate one or more of the plurality of pumping or metering devices based on the nutritive level recipe to dispense the amount of the one or more sweeteners.

In some implementations of the beverage dispenser, the nutritive level recipe comprises an amount of a plurality of sweeteners to be dispensed to produce the beverage at the selected nutritive level.

In some implementations of the beverage dispenser, the pumping or metering devices include one or more of a positive displacement pump, a static mechanical control valve, and a dynamic mechanical control valve.

In some implementations of the beverage dispenser, the controller is further configured to look up a beverage recipe for the beverage, the beverage recipe comprises amounts of a plurality of ingredients other than the one or more sweeteners to be dispensed to produce the beverage. The nutritive level recipe and the beverage recipe may be maintained in a combined recipe. The plurality of ingredients comprise one or more non-sweetener micro-ingredients, macro-ingredients, and/or diluents.

In some implementations of the beverage dispenser, the nutritive level recipe is maintained in a table of a plurality of recipes, each of the plurality of recipes comprises an amount of one or more sweeteners to be dispensed to produce the beverage at different nutritive level. One or more of the plurality of recipes comprises a different combination of one or more sweeteners than the nutritive level recipe.

In some implementations of the beverage dispenser, the one or more sweeteners comprise a plurality of sweeteners including one or more caloric sweeteners and one or more non-caloric sweeteners.

In some implementations of the beverage dispenser, the user interface is further configured to receive a selection of a second beverage to be dispensed at the nutritive level, wherein a second nutritive level recipe comprises a second amount of one or more sweeteners to be dispensed to produce the second beverage at the selected nutritive level.

Aspects of the disclosure provide a method of dispensing a beverage from a beverage dispenser. The method comprises receiving, at a user interface of the beverage dispenser, a selection of the beverage to be dispensed and a selection of a nutritive level for the beverage. The method also comprises looking up a nutritive level recipe based on the nutritive level selection, the nutritive level recipe comprises an amount of one or more sweeteners to be dispensed to produce the beverage at the selected nutritive level. The method also comprises activating one or more of a plurality of pumping or metering devices on the beverage dispenser based on the nutritive level recipe to dispense the amount of the one or more sweeteners via a nozzle.

In some implementations of the method, the nutritive level recipe comprises an amount of a plurality of sweeteners to be dispensed to produce the beverage at the selected nutritive level.

In some implementations of the method, the pumping or metering devices include one or more of a positive displacement pump, a static mechanical control valve, and a dynamic mechanical control valve.

In some implementations, the method further comprises looking up a beverage recipe for the beverage, the beverage recipe comprises amounts of a plurality of ingredients other than the one or more sweeteners to be dispensed to produce the beverage. The plurality of ingredients comprise one or more non-sweetener micro-ingredients, macro-ingredients, and/or diluents.

In some implementations of the method, the nutritive level recipe and the beverage recipe are maintained in a combined recipe.

In some implementations of the method, the nutritive level recipe is maintained in a table of a plurality of recipes, each of the plurality of recipes comprises an amount of one or more sweeteners to be dispensed to produce the beverage at different nutritive level. One or more of the plurality of recipes comprises a different combination of one or more sweeteners than the nutritive level recipe.

In some implementations of the method, the one or more sweeteners comprise a plurality of sweeteners including one or more caloric sweeteners and one or more non-caloric sweeteners.

In some implementations, the method further comprises receiving, at a user interface of the beverage dispenser, a selection of a second beverage to be dispensed at the nutritive level, wherein a second nutritive level recipe comprises a second amount of one or more sweeteners to be dispensed to produce the second beverage at the selected nutritive level.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 3 illustrates an exemplary look-up table that associates a nutritive level with a plurality of sweetener sources for a given brand or type of beverage suitable for implementing the several embodiments of the disclosure.

FIG. 4 illustrates an exemplary look-up table that associates a nutritive level with a plurality of sweetener sources and other ingredient sources in a beverage recipe suitable for implementing the several embodiments of the disclosure.

DETAILED DESCRIPTION

Figures 1, 2:
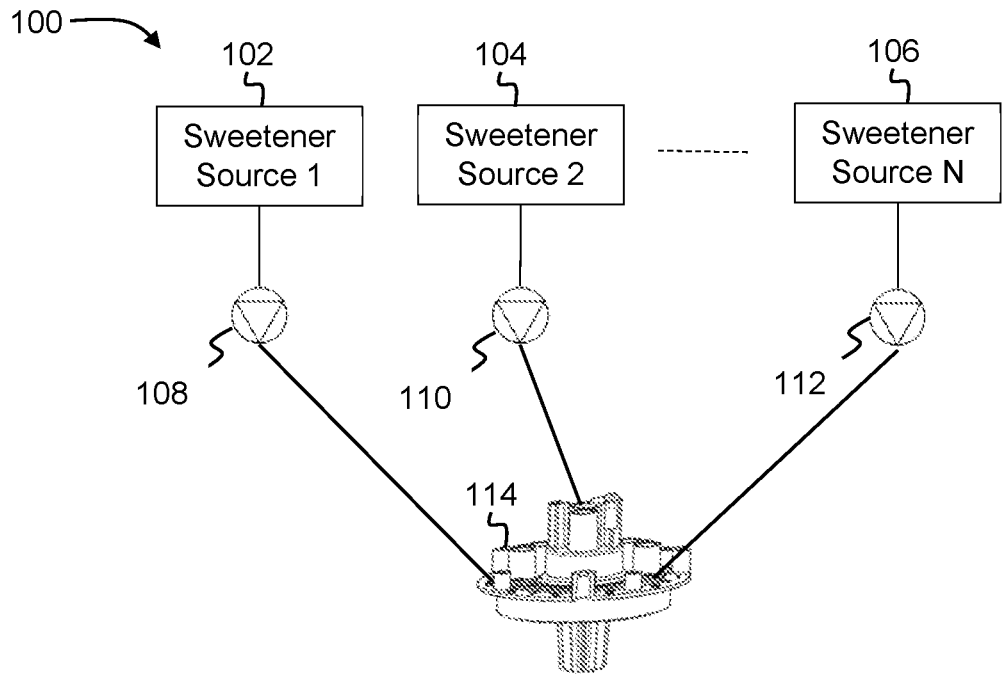
FIG. 1 illustrates an exemplary block diagram a beverage dispenser with selectable nutritive levels according to various embodiments of the disclosure.
FIG. 2 illustrates an exemplary look-up table that associates a nutritive choice, a corresponding caloric level, and a nutritive level suitable for implementing the several embodiments of the disclosure.

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents. Use of the phrase "and/or" indicates that any one or any combination of a list of options can be used. For example, "A, B, and/or C" means "A", or "B", or "C", or "A and B", or "A and C", or "B and C", or "A and B and C".

Typically, consumers may be able to select between regular and diet versions of a product on a product dispenser. However, consumers are increasingly desiring more choice in the products that they consume. In some food product dispensers, such as a beverage dispenser, consumers may be able to customize the amount of various ingredients to be dispensed in a product. However, such wide selection may frequently result in undesirable flavors or combinations of flavors in the dispensed product, leading to wasted product and unsatisfactory consumer experience.

The dispenser of the pending disclosure is configured to dispense food products at varying nutritive levels by dispensing a combination of sweeteners in a predetermined ratio from a plurality of sweetener sources. Using a predetermined combination of sweeteners in a predetermined ratio for a selected nutritive level for a given product ensures that the dispensed product will have a desirable flavor profile while at the same time providing increased consumer choice of the amount of calories consumed and the type of sweeteners used. Some of the plurality of sweeteners may be zero calorie sweeteners, while others may be caloric sweeteners, mid-calorie sweeteners, or low-calorie sweeteners. A combination of caloric, mid-calorie, low calorie, and/or non-caloric sweeteners may be dispensed to produce a food product with a specified caloric level or nutritive level. For the purpose of this disclose, a caloric sweetener may have 60 to 100 or more calories per ounce, though typically around 80 calories per ounce. A mid-calorie sweetener may have between 30 to 60 calories per ounce. A low-calorie sweetener may have 10 to 30 or less calories per ounce. A non-caloric sweetener may have about zero calories per ounce.

For a given nutritive level selected, the product dispenser may dispense different combinations of sweeteners and/or different ratios of sweeteners for different brands or products to be dispensed. Likewise, for a given brand or product, the product dispenser may dispense different combinations of sweeteners and/or different ratios of sweeteners for different selected nutritive levels. Accordingly, the product dispenser of the pending disclosure facilitates increased consumer choice through selectable nutritive levels for a food product dispensed at a dispenser. At the same time, the product dispenser automatically adapts the taste profile of the finished product by dispensing a combination of sweeteners at predetermined ratios to satisfy the nutritive level selection and ensure a consistent and quality finished product.

In various embodiments of the disclosure, the food product is a beverage and the dispenser is a beverage dispenser. While the pending disclosure is described throughout with reference to a beverage dispenser, any other food dispenser or comestible product dispenser may be used. The beverage dispenser receives a selection of a beverage to be dispensed by the beverage dispenser. The beverage dispenser also receives a selection of a desired nutritive level of the beverage to be dispense. The nutritive level selection may be received via selection on a user interface of the beverage dispenser or via a profile received at the beverage dispenser with a preference for a nutritive level. For example, the profile may be received at the beverage dispenser as described in commonly owned U.S. patent application Ser. No. 14/445,252, entitled "Facilitating Individualized User Interaction with an Electronic Device," filed Feb. 5, 2015, hereby incorporated by reference in its entirety. Other methods of consumer interactions for receiving a user profile, customizing a beverage formulation, or otherwise receiving a selection of a desired sweetener, caloric level, or nutritive level may be used, such as described in commonly owned U.S. Pat. No. 9,051,162, entitled "System and Methods for Facilitating Consumer-Dispenser Interactions," filed Sep. 4, 2008, or commonly owned U.S. patent application Ser. No. 15/564,239, entitled "System and method for producing a customized Beverage or Beverage Concentrate," filed Oct. 4, 2017, the disclosures of which are both hereby incorporated by reference in their entirety.

The beverage dispenser looks up a beverage recipe for the selected beverage and a sweetener recipe for the selected nutritive level. The sweetener recipe for the selected nutritive level may be based on the selected beverage. That is a different sweetener recipe may be used for different beverages at the same nutritive level to account for the flavor profile differences of the different beverages. Each of the beverage recipe and the sweetener recipe may specify a plurality of ingredients in a predetermined ratio. At one or more nutritive levels for a given product, the sweetener recipe may specify a single sweetener ingredient. The beverage dispenser activates pumping or metering devices associated with each of the ingredients in the beverage recipe and the sweetener recipe to dispense the ingredients in the predetermined ratio to dispense a finished beverage with the selected nutritive level.

Described herein are example systems and methods for controlling a blended sweetener flow in a beverage dispensing system (such as a Coca-Cola® Freestyle®, traditional fountain dispenser, or traditional fountain dispenser with micro-ingredients). For example, a beverage dispensing system (which may include one or more macro-ingredients and one or more micro-ingredients) combines macro-ingredients (such as sweeteners, water, or carbonated water) and micro-ingredients (such as high intensity sweeteners, flavorings, food acids, or additives) to create a finished beverage. Such micro-dosing functionality may increase the dispensing capabilities of the beverage dispensing system to deliver a large variety of beverages and improve the quality of the beverage dispensed by the beverage dispensing system.

Generally described, the macro-ingredients may have reconstitution ratios in the range from full strength (no dilution) to about six (6) to one (1) (but generally less than about ten (10) to one (1)). As used herein, the reconstitution ratio refers to the ratio of diluent (e.g., water or carbonated water) to beverage ingredient. Therefore, a macro-ingredient with a 5:1 reconstitution ratio refers to a macro-ingredient that is to be dispensed and mixed with five parts diluent for every part of the macro-ingredient in the finished beverage. Many macro-ingredients may have reconstitution ratios in the range of about 3:1 to 5.5:1, including 4.5:1, 4.75:1, 5:1, 5.25:1, 5.5:1, and 8:1 reconstitution ratios.

The macro-ingredients may include sweeteners such as sugar syrup, HFCS ("High Fructose Corn Syrup"), FIS ("Fully Inverted Sugar"), MIS ("Medium Inverted Sugar"), mid-calorie sweeteners comprised of nutritive and non-nutritive or high intensity sweetener blends, and other such nutritive sweeteners that are difficult to pump and accurately meter at concentrations greater than about 10:1—particularly after having been cooled to standard beverage dispensing temperatures of around 35-45° F. An erythritol sweetener may also be considered a macro-ingredient sweetener when used as the primary sweetener source for a beverage, though typically erythritol will be blended with other sweetener sources and used in solutions with higher reconstitution ratios such that it may be considered a micro-ingredient as described below.

The macro-ingredients may also include traditional BIB ("bag-in-box") flavored syrups (e.g., COCA-COLA bag-in-box syrup) which contain all of a finished beverage's sweetener, flavors, and acids that when dispensed is to be mixed with a diluent source such as plain or carbonated water in ratios of around 3:1 to 6:1 of diluent to the syrup. Other typical macro-ingredients may include concentrated extracts, purees, juice concentrates, dairy products or concentrates, soy concentrates, and rice concentrates.

The macro-ingredient may also include macro-ingredient base products. Such macro-ingredient base products may include the sweetener as well as some common flavorings, acids, and other common components of a plurality of different finished beverages. However, one or more additional beverage ingredients (either micro-ingredients or macro-ingredients as described herein) other than the diluent are to be dispensed and mix with the macro-ingredient base product to produce a particular finished beverage. In other words, the macro-ingredient base product may be dispensed and mixed with a first micro-ingredient non-sweetener flavor component to produce a first finished beverage. The same macro-ingredient base product may be dispensed and mixed with a second micro-ingredient non-sweetener flavor component to produce a second finished beverage.

The macro-ingredients described above may be stored in a conventional bag-in-box container in, at and/or remote from the dispenser. The viscosity of the macro-ingredients may range from about 1 to about 10,000 centipoise and generally over 100 centipoises or so when chilled. Other types of macro-ingredients may be used herein.

The micro-ingredients may have reconstitution ratios ranging from about ten (10) to one (1) and higher. Specifically, many micro-ingredients may have reconstitution ratios in the range of about 20:1, to 50:1, to 100:1, to 300:1, or higher. The viscosities of the micro-ingredients typically range from about one (1) to about six (6) centipoise or so, but may vary from this range. In some instances, the viscosities of the micro-ingredients may be forty (40) centipoise or less. Examples of micro-ingredients include natural or artificial flavors; flavor additives; natural or artificial colors; artificial sweeteners (high potency, nonnutritive, or otherwise); antifoam agents, nonnutritive ingredients, additives for controlling tartness, e.g., citric acid or potassium citrate; functional additives such as vitamins, minerals, herbal extracts, nutraceuticals; and over the counter (or otherwise) medicines such as pseudoephedrine, acetaminophen; and similar types of ingredients. Various acids may be used in micro-ingredients including food acid concentrates such as phosphoric acid, citric acid, malic acid, or any other such common food acids. Various types of alcohols may be used as either macro- or micro-ingredients. The micro-ingredients may be in liquid, gaseous, or powder form (and/or combinations thereof including soluble and suspended ingredients in a variety of media, including water, organic solvents, and oils). Other types of micro-ingredients may be used herein.

Typically, micro-ingredients for a finished beverage product include separately stored non-sweetener beverage component concentrates that constitute the flavor components of the finished beverage. Non-sweetener beverage component concentrates do not act as a primary sweetener source for the finished beverage and do not contain added sweeteners, though some non-sweetener beverage component concentrates may have sweet tasting flavor components or flavor components that are perceived as sweet in them. These non-sweetener beverage component concentrates may include the food acid concentrate and food acid-degradable (or non-acid) concentrate components of the flavor, such as described in commonly owned U.S. patent application Ser. No. 11/276,553, entitled "Methods and Apparatus for Making Compositions Comprising and Acid and Acid Degradable Component and/or Compositions Comprising a Plurality of Selectable Components," which is herein incorporated by reference in its entirety. As noted above, micro-ingredients may have reconstitution ratios ranging from about ten (10) to one (1) and higher, where the micro-ingredients for the separately stored non-sweetener beverage component concentrates that constitute the flavor components of the finished beverage typically have reconstitution ratios ranging from 50:1, 75:1, 100:1, 150:1, 300:1, or higher.

For example, the non-sweetener flavor components of a cola finished beverage may be provided from separately stored first non-sweetener beverage component concentrate and a second non-sweetener beverage component concentrate. The first non-sweetener beverage component concentrate may comprise the food acid concentrate components of the cola finished beverage, such as phosphoric acid. The second non-sweetener beverage component concentrate may comprise the food acid-degradable concentrate components of the cola finished beverage, such as flavor oils that would react with and impact the taste and shelf life of a non-sweetener beverage component concentrate were they to be stored with the phosphoric acid or other food acid concentrate components separately stored in the first non-sweetener component concentrate. While the second non-sweetener beverage component concentrate does not include the food acid concentrate components of the first non-sweetener beverage component concentrate (e.g., phosphoric acid), the second non-sweetener beverage component concentrate may still be a high-acid beverage component solution (e.g., pH less than 4.6).

A finished beverage may have a plurality of non-sweetener concentrate components of the flavor other than the acid concentrate component of the finished beverage. For example, the non-sweetener flavor components of a cherry cola finished beverage may be provided from the separately stored non-sweetener beverage component concentrates described in the above example as well as a cherry non-sweetener component concentrate. The cherry non-sweetener component concentrate may be dispensed in an amount consistent with a recipe for the cherry cola finished beverage. Such a recipe may have more, less, or the same amount of the cherry non-sweetener component concentrate than other recipes for other finished beverages that include the cherry non-sweetener component concentrate. For example, the amount of cherry specified in the recipe for a cherry cola finished beverage may be more than the amount of cherry specified in the recipe for a cherry lemon-lime finished beverage to provide an optimal taste profile for each of the finished beverage versions. Such recipe-based flavor versions of finished beverages are to be contrasted with the addition of flavor additives or flavor shots as described below.

Other typical micro-ingredients for a finished beverage product may include micro-ingredient sweeteners. Micro-ingredient sweeteners may include high intensity sweeteners such as aspartame, Ace-K, steviol glycosides (e.g., Reb A, Reb M), sucralose, saccharin, or combinations thereof. Micro-ingredient sweeteners may also include erythritol when dispensed in combination with one or more other sweetener sources or when using blends of erythritol and one or more high intensity sweeteners as a single sweetener source.

Other typical micro-ingredients for supplementing a finished beverage product may include micro-ingredient flavor additives. Micro-ingredient flavor additives may include additional flavor options that can be added to a base beverage flavor. The micro-ingredient flavor additives may be non-sweetener beverage component concentrates. For example, a base beverage may be a cola flavored beverage, whereas cherry, lime, lemon, orange, and the like may be added to the cola beverage as flavor additives, sometimes referred to as flavor shots. In contrast to recipe-based flavor versions of finished beverages, the amount of micro-ingredient flavor additive added to supplement a finished beverage may be consistent among different finished beverages. For example, the amount of cherry non-sweetener component concentrate included as a flavor additive or flavor shot in a cola finished beverage may be the same as the amount of cherry non-sweetener component concentrate included as a flavor additive or flavor shot in a lemon-lime finished beverage. Additionally, whereas a recipe-based flavor version of a finished beverage is selectable via a single finished beverage selection icon or button (e.g., cherry cola icon/button), a flavor additive or flavor shot is a supplemental selection in addition to the finished beverage selection icon or button (e.g., cola icon/button selection followed by a cherry icon/button selection).

As is generally understood, such beverage selections may be made through a touchscreen user interface or other typical beverage user interface selection mechanism (e.g., buttons) on a beverage dispenser. The selected beverage, including any selected flavor additives, may then be dispensed upon the beverage dispenser receiving a further dispense command through a separate dispense button on the touchscreen user interface or through interaction with a separate pour mechanism such as a pour button (electromechanical, capacitive touch, or otherwise) or pour lever.

In the traditional BIB flavored syrup delivery of a finished beverage, a macro-ingredient flavored syrup that contains all of a finished beverage's sweetener, flavors, and acids is mixed with a diluent source such as plain or carbonated water in ratios of around 3:1 to 6:1 of diluent to the syrup. In contrast, for a micro-ingredient delivery of a finished beverage, the sweetener(s) and the non-sweetener beverage component concentrates of the finished beverage are all separately stored and mixed together about a nozzle when the finished beverage is dispensed. Example nozzles suitable for dispensing of such micro-ingredients include those described in commonly owned U.S. provisional patent application Ser. No. 62/433,886, entitled "Dispensing Nozzle Assembly," PCT patent application Ser. No. PCT/US15/026657, entitled "Common Dispensing Nozzle Assembly," U.S. Pat. No. 7,866,509, entitled "Dispensing Nozzle Assembly," or U.S. Pat. No. 7,578,415, entitled "Dispensing Nozzle Assembly," which are all herein incorporated by reference in their entirety.

In operation, the beverage dispenser may dispense finished beverages from any one or more of the macro-ingredient or micro-ingredient sources described above. For example, similar to the traditional BIB flavored syrup delivery of a finished beverage, a macro-ingredient flavored syrup may be dispensed with a diluent source such as plain or carbonated water to produce a finished beverage. Additionally, the traditional BIB flavored syrup may be dispensed with the diluent and one or more micro-ingredient flavor additives to increase the variety of beverages offered by the beverage dispenser.

Micro-ingredient-based finished beverages may be dispensed by separately dispensing each of the two or more non-sweetener beverage component concentrates of the finished beverage along with a sweetener and diluent. The sweetener may be a macro-ingredient sweetener and/or a micro-ingredient sweetener and the diluent may be water and/or carbonated water. For example, a micro-ingredient-based cola finished beverage may be dispensed by separately dispensing food acid concentrate components of the cola finished beverage, such as phosphoric acid, food acid-degradable concentrate components of the cola finished beverage, such as flavor oils, macro-ingredient sweetener, such as HFCS, and carbonated water. In another example, a micro-ingredient-based diet-cola finished beverage may be dispensed by separately dispensing food acid concentrate components of the diet-cola finished beverage, food acid-degradable concentrate components of the diet-cola finished beverage, micro-ingredient sweetener, such as aspartame or an aspartame blend, and carbonated water.

As a further example, a mid-calorie micro-ingredient-based cola finished beverage may be dispensed by separately dispensing food acid concentrate components of the mid-calorie cola finished beverage, food acid-degradable concentrate components of the mid-calorie cola finished beverage, a reduced amount of a macro-ingredient sweetener, a reduced amount of a micro-ingredient sweetener, and carbonated water. By reduced amount of macro-ingredient and micro-ingredient sweeteners, it is meant to be in comparison with the amount of macro-ingredient or micro-ingredient sweetener used in the cola finished beverage and diet-cola finished beverage.

As a final example, a supplemental flavored micro-ingredient-based beverage, such as a cherry cola beverage or a cola beverage with an orange flavor shot, may be dispensed by separately dispensing a food acid concentrate components of the flavored cola finished beverage, food acid-degradable concentrate components of the flavored cola finished beverage, one or more non-sweetener micro-ingredient flavor additives (dispensed as either as a recipe-based flavor version of a finished beverage or a flavor shot), a sweetener (macro-ingredient sweetener, micro-ingredient sweetener, or combinations thereof), and carbonated water. While the above examples are provided for carbonated beverages, they apply to still beverages as well by substituting carbonated water with plain water.

The various ingredients may be dispensed by the beverage dispenser in a continuous pour mode where the appropriate ingredients in the appropriate proportions (e.g., in a predetermined ratio) for a given flow rate of the beverage being dispensed. In other words, as opposed to a conventional batch operation where a predetermined amount of ingredients are combined, the beverage dispenser provides for continuous mixing and flows in the correct ratio of ingredients for a pour of any volume. This continuous mix and flow method can also be applied to the dispensing of a particular size beverage selected by the selection of a beverage size button by setting a predetermined dispensing time for each size of beverage.

FIG. 1 illustrates an exemplary block diagram a beverage dispenser 100 with selectable nutritive levels according to various embodiments of the disclosure. The beverage dispenser 100 is configured to receive a plurality of sweetener sources, such as sweetener source 102, 104, and 106. Each of the sweetener sources 102, 104, and 106 may supply a micro-ingredient sweetener or a macro-ingredient sweetener, described in more detail below. One or more of the sweetener sources 102, 104, and 106 may be housed within the beverage dispenser 100 and/or located outside the beverage dispenser 100 either adjacent to (e.g., under the counter or otherwise within about 10 feet) or remote from (e.g., in a back room or otherwise located farther than 10 feet away) the beverage dispenser 100.

Each of the sweetener sources 102, 104, and 106 is in fluidic communication with a corresponding one of the pumping or metering devices 108, 110, 112. For example, sweetener source 102 is in fluidic communication with pumping or metering device 108. Likewise, sweetener sources 104, 106 are in fluidic communication with corresponding pumping or metering devices 110, 112. Each of the pumping or metering devices 108, 110, 112 is in fluidic communication with a nozzle 114. The pumping or metering devices 108, 110, 112 are configured to meter out a sweetener ingredient according to a nutritive level recipe of a selected nutritive level for a selected beverage. The nozzle 114 is configured to dispense and mix a plurality of sweetener ingredients to form a finished beverage.

FIG. 2 illustrates an exemplary look-up table 200 that associates a nutritive choice 202, a corresponding caloric level 204, and a nutritive level 206. For example, the nutritive choice of a "Regular" beverage may have a corresponding caloric level of 60-100 calories per 8 ounce serving, and a corresponding nutritive level $NL_1$. The nutritive choice is a descriptor of the corresponding nutritive level that may be displayed on a user interface of the beverage dispenser or otherwise provided as a selectable option for a user of the beverage dispenser. The nutritive choice of a "Mid-Cal" beverage may have a corresponding caloric level of 30-60 calories per 8 ounce serving, and a corresponding nutritive level $NL_2$. The nutritive choice of a "Low-Cal" beverage may have a corresponding caloric level of 10-30 calories per 8 ounce serving, and a corresponding nutritive level $NL_3$. The nutritive choice of a "Diet" beverage may have a corresponding caloric level of less than 10 calories per 8 ounce serving, and a corresponding nutritive level $NL_4$. The above caloric ranges are merely exemplary and other, more, or less ranges may be used. Other nutritive choice descriptors may be used.

The nutritive choice 202 in the look-up table 200 corresponds to the nutritive level selection received by the beverage dispenser 100. The caloric level 204 may be displayed by the beverage dispenser 100 prior to or after receiving the nutritive level selection. The nutritive level 206 may be used as a key to locate the corresponding nutritive level recipe for the selected beverage. In some implementations, the nutritive level recipes for each of the nutritive levels are the same for all beverages dispensed by the beverage dispenser 100.

FIG. 3 illustrates an exemplary look-up table 300 that associates a nutritive level 206 with a plurality of sweetener sources 302-310 for a given brand or type of beverage. For a given nutritive level, the look-up table 300 specifies a flow rate for each of plurality of sweetener sources or a ratio of each of a plurality of sweetener sources to other ingredients of a beverage for a given flow rate of the beverage. For example, as shown in FIG. 3, for nutritive level $NL_1$, the look-up table 300 specifies a flow rate of X for sweetener source $S_1$ and a flow rate of Z for a sweetener source $S_3$. The beverage dispenser 100 uses the values in the look-up table 300 to control the operation of a plurality of the pumping or metering devices 108, 110, 112 so as to dispense a beverage with a selected nutritive level. For example, a pumping or metering device associated with sweetener source $S_1$ may be operated to dispense the sweetener in sweetener source $S_1$ at the flow rate Z. While described above as a flow rate, any other measure of an amount of an ingredient to be dispensed may be used.

As shown in FIG. 3, some nutritive levels may have a greater number of sweetener sources than other nutritive levels. A given nutritive level may have one, two, three, four, five, or more sweetener sources associated with the nutritive level. For example, as shown in FIG. 3, nutritive level $NL_1$ has two associated sweetener sources, while nutritive level $NL_2$ has three associated sweetener sources.

Additionally, for different nutritive levels, the look-up table 300 may specify the same flow rates for different sweetener sources. For example, nutritive level $NL_1$ specifies a flow rate of X for sweetener source $S_1$ and a flow rate of Z for sweetener source $S_3$, while nutritive level $NL_n$ specifies a flow rate of X for $S_4$ and a flow rate of Z for sweetener source $S_n$.

Similarly, for different nutritive levels, the look-up table 300 may specify different flow rates for different sweetener sources. For example, nutritive level $NL_2$ specifies a flow rate of Y for sweetener source $S_1$, a flow rate of Z for sweetener source $S_2$, and a flow rate of Z for sweetener source $S_4$, while nutritive level $NL_3$ specifies a flow rate of Z for sweetener source $S_1$, a flow rate of Y for sweetener source $S_2$, and a flow rate of X for sweetener source $S_n$.

As shown in the above example, the same sweetener source may be used in different nutritive levels, but at different flow rates in the different nutritive levels. For example, for sweetener source $S_1$, the nutritive level $NL_2$ has a flow rate of Y while the nutritive level $NL_3$ has a flow rate of Z. While a plurality of sweetener sources is specified for each of the nutritive levels in the look-up table shown in FIG. 3, in some implementations, one or more nutritive levels may only have a single associated sweetener source.

The look-up table 300 specifies the combinations of sweeteners and the flow rate of each sweetener in the combination for a given brand or type of beverage dispensed by the beverage dispenser 100. Other brands or types of beverages may use different combinations of sweeteners or the same combinations of sweeteners at different flow rates. Each brand or type of beverage may have a separate look-up table. Therefore, the beverage dispenser 100 may adapt the sweeteners or flow rate of the sweeteners to the flavor profile of the beverage being dispensed.

In some implementations, rather than having a separate nutritive level recipe for each brand or type of beverage, such as look-up table 300, the beverage dispenser may incorporate the nutritive level recipe in a beverage recipe 400, such as shown in FIG. 4. The look-up table 400 associates a nutritive level 206 with a plurality of sweetener sources 302, 304, 308, and 402-406, with one or more flavor ingredients 408-410, and optionally one or more additives 412-414. The flavor ingredients 408-410 and/or additives 412-414 and associated flow rates may be the same for different nutritive levels. In some implementations, the flow rate of one or more of the flavor ingredients 408-410 may be different for different nutritive levels based on the combination of sweeteners used.

In addition to the above, consumers may have preferences for different types of sweeteners. For example, for mid-calorie, low calorie, and/or non-caloric sweeteners or sweetener blends a particular consumer may have a preference for a steviol glycoside sweetener over an aspartame, Ace-K, sucralose, or saccharin sweetener. In contrast, another consumer may have a preference for the flavor profile of aspartame and/or Ace-K. This consumer preference for different types of sweeteners may also be expressed in terms of sweeteners that the consumer does not like. For example, a consumer may have a preference for not having a beverage with a saccharin sweetener, but no active preference for a different type of sweetener.

To accommodate consumer preferences for different types of sweeteners, the look-up tables 300 and 400 described above may include multiple nutritive level rows that provide approximately the same nutritive level range (e.g., within the calorie ranges shown in FIG. 2), but are composed of different combinations of sweeteners to further accommodate consumer preferences for one or more particular sweeteners.

In some implementations, a consumer preference for a particular sweetener (either to include or to avoid in a dispensed beverage) may limit an available set of selectable beverages to a subset of beverages that correspond with the consumer preference. For example, based on the flavor profile of certain sweeteners, those sweeteners may only be used in the subset of beverages where the finished beverage has a desirable finished flavor profile. In other words, a sweetener may have a flavor profile that conflicts with the flavor profile of a particular finished beverage. Therefore, upon selection of a preference to include the sweetener, the option to select the particular finished beverage may be removed. In addition to conflicting flavor profiles, other properties of sweeteners, such as foaming characteristics, likelihood of forming a precipitate or crystallizing in a finished beverage, or the like, may limit the available set of selectable beverages to a subset of beverages.

While the examples provided above are focused on preferences for low- or no-calorie sweeteners, the same follows for mid- or regular calorie sweeteners. For example, consumer preferences may exist for a cane-sugar sweetener or inverted sugar sweetener over a high-fructose corn syrup sweetener. Other such sweetener preferences are contemplated by this disclosure.

Figure 5:
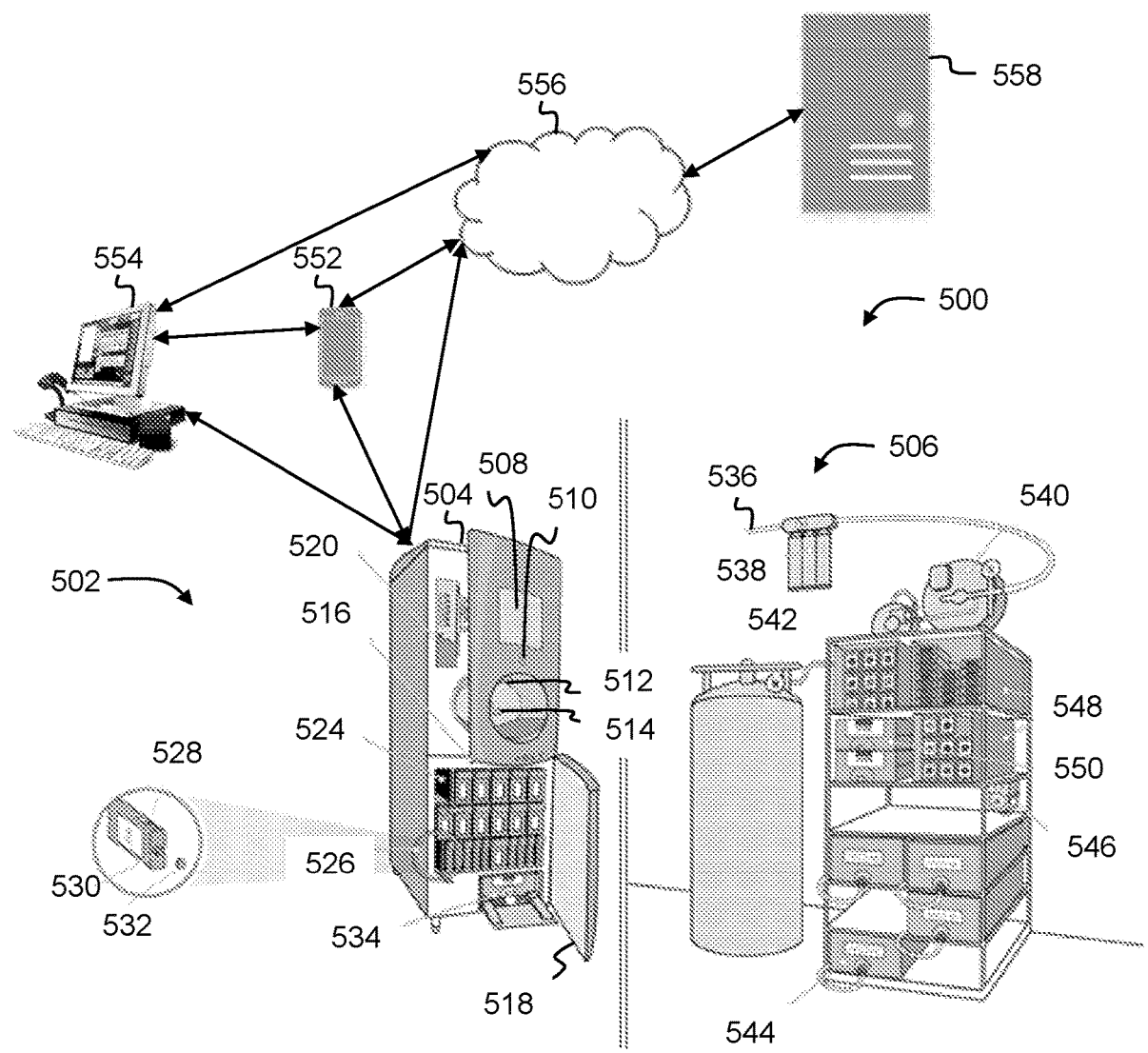
FIG. 5 illustrates an exemplary beverage dispenser system suitable for implementing the several embodiments of the disclosure.

FIG. 5 illustrates an exemplary beverage dispenser system 500 suitable for implementing the several embodiments of the disclosure. As shown, the beverage dispenser system 500 is configured as an ice cooled beverage dispenser. Other configurations of beverage dispensers are contemplated by this disclosure such as a drop-in ice-cooled beverage dispenser, a counter electric beverage dispenser, a remote recirculation beverage dispenser, or any other beverage dispenser configuration.

The beverage dispenser system 500 includes a front room system 502 with a beverage dispenser 504 and a back-room system 506. The beverage dispenser 504 includes a user interface 508, such as a touchscreen display, to facilitate selection of the beverage to be dispensed. The user interface 508 may employ various screens to facilitate user interactions on the beverage dispenser 504 and/or receive a user profile through interaction with a user's mobile device 552, such as described in commonly owned U.S. patent application Ser. No. 14/485,826, entitled "Product Categorization User Interface for a Dispensing Device," which is herein incorporated by reference in its entirety.

Upon receiving a beverage selection via the user interface 508, a pour button 510 may be activated to dispense the selected beverage from the beverage dispenser 504 via a nozzle 514. For example, the pour button 510 may be an electromechanical button, capacitive touch button, or other button selectable by a user to activate the beverage dispenser 504 to dispense a beverage. While shown as a button, the pour button 510 may alternatively be implemented as a lever or other mechanism for activating the beverage dispenser 504 to dispense a beverage. As shown in FIG. 5, the pour button 510 is separate from the user interface 508. In some implementations, the pour button 510 may be implemented as a selectable icon in the user interface 508.

In some implementations, the beverage dispenser may also include an ice lever 514. Upon being activated, the ice lever 514 may cause the beverage dispenser 504 to dispense ice through an ice chute (not shown). For beverage dispensers that do not have an ice bin, such as counter-electric or remote recirculation beverage dispensers, the ice lever 514 may be omitted.

The beverage dispenser 504 may be secured via a primary door 516 and an ingredient door 518. The primary door 516 and the ingredient door 518 may be secured via one or more locks. In some implementations, the locks are a lock and key. In some implementations, the lock on the ingredient door 518 may be opened via an RFID reader (not shown) reading an authorize ingredient package 528. The primary door 516 may secure electronic components of the beverage dispenser 504 including one or more controllers 520. The ingredient door 518 may secure an ingredient compartment that houses an ingredient matrix 524.

The ingredient matrix 524 includes a plurality of slots 526 for receiving ingredient packages 528. In various implementations, the ingredient packages 528 may be micro-ingredient cartridges. The micro-ingredient cartridges may be single cartridges or double cartridges, such as described in commonly owned U.S. patent application Ser. No. 14/209,684, entitled "Beverage Dispenser Container and Carton," and U.S. patent application Ser. No. 12/494,427, entitled "Container Filling Systems and Methods," which are both herein incorporated by reference in their entirety. As shown in FIG. 5, there are three drawers of ingredients in the ingredient matrix 524. One or more of the drawers may slide back and forth along a rail so as to periodically agitate the ingredients housed on the drawer. Other configurations of the ingredient matrix 524 are possible, such as via one or more static and/or agitated ingredient towers.

Each ingredient package 528 may comprise an RFID tag, a fitment 530, and a fitment seal 532. The fitment seal 532 may be removed prior to installation into the beverage dispenser 504. Upon installation, the fitment 530 may engage with and provide a fluidic communication between a probe (not shown) in the slot 526 and the ingredients contained in the ingredient package 528. The ingredient matrix 524 may also contain one or more large volume micro-ingredient packages 534, such as for one or more micro-ingredient sweetener sources.

The beverage dispenser 504 may also include a carbonator (not shown) for receiving water and carbon dioxide to produce carbonated water. The beverage dispenser 504 may also include one or more heat exchangers (not shown), such as a cold plate, for cooling one or more of the beverage ingredients contained in or received by the beverage dispenser 504. In some implementations, one or more of the micro-ingredients dispensed via the nozzle 512 are not cooled via the heat exchanger or are otherwise maintained at an ambient temperature. Macro-ingredients dispensed via the nozzle 512 are typically cooled via the heat exchanger prior to being dispensed.

The back-room system 506 is typically located in a back room remote from the front room system 502, such as a storage area in a merchant location. The back-room system 506 includes a water source 536 such as a municipal water supply that provides a pressurized source of plain water. The water received via the water source 536 may be filtered or otherwise treated by a water treatment system 538. The treated water may optionally be pressurized to a desired pressure with a water booster 540 and supplied to the beverage dispenser. A carbon dioxide source 542 may supply carbon dioxide to the beverage dispenser 504.

One or more macro-ingredient sources 544 may be located in the back room. The macro-ingredient from each macro-ingredient source 544 may be supplied to the beverage dispenser 504 via a pump 546. The pump 546 may be a controlled gear pump, diaphragm pump, BIB pump, or any other suitable pump for supplying macro-ingredients to the beverage dispenser 504. The back-room system 506 may also include a rack with one or more storage locations 548 for spare micro-ingredients and one or more storage locations 550 for spare macro-ingredients.

The beverage dispenser 504 may include one or more network interfaces for communicating directly with devices in the front room or the back room, communicating with devices in the front room or the back room in a local area network (LAN), or communicating with devices remote from a location with the beverage dispenser system 500 via a wide area network (WAN) connection. For example, the beverage dispenser 504 may include networking devices such as a near field communication (NFC) module, a BLUETOOTH module, a WiFi module, a cellular modem, an Ethernet module, and the like. The beverage dispenser 504 may communicate via a direct communication or via a LAN with a user's mobile device 552 or a point-of-sale (POS) device 554 to receive a beverage selection or user profile of a user for configuring the beverage dispenser 504 to dispense one or more beverages based on the beverage selection or user profile. The user profile may include stored favorite beverages for the user, mixed or blended beverages created or stored by the user in their profile, and/or one or more beverage preferences, such as preferred nutritive level. The beverage dispenser 504 may also communicate via a WAN 556 for communicating with one or more remote servers 558 to receive software updates, content updates, user profiles, or beverage selections made via the remote server 558.

Figure 6:
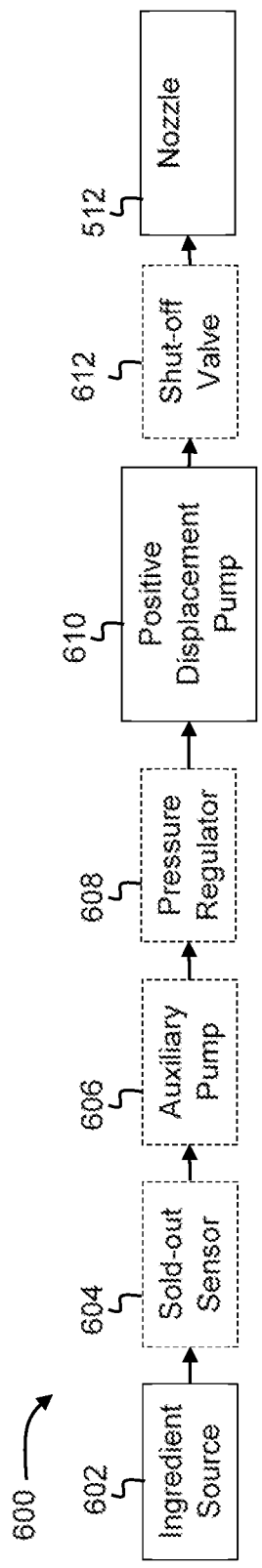
FIG. 6 illustrates an exemplary fluidic circuit with a positive displacement pump suitable for implementing the several embodiments of the disclosure.
Figure 7:
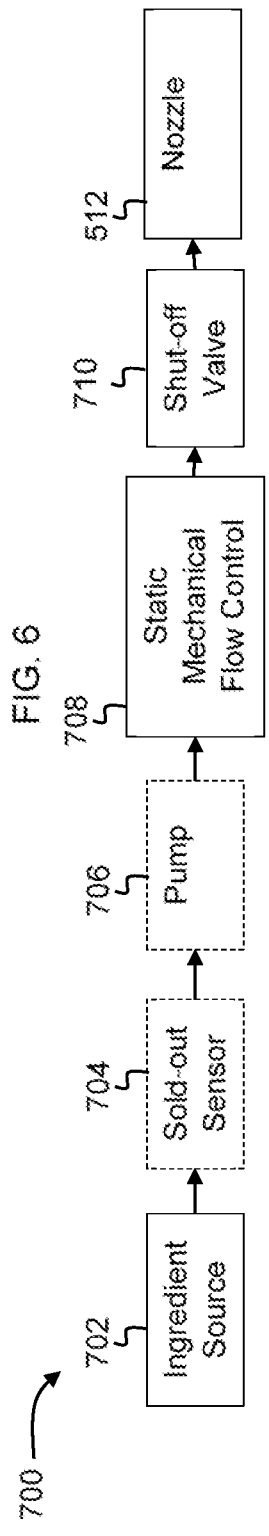
FIG. 7 illustrates an exemplary fluidic circuit with a static mechanical flow control suitable for implementing the several embodiments of the disclosure.
Figure 8:
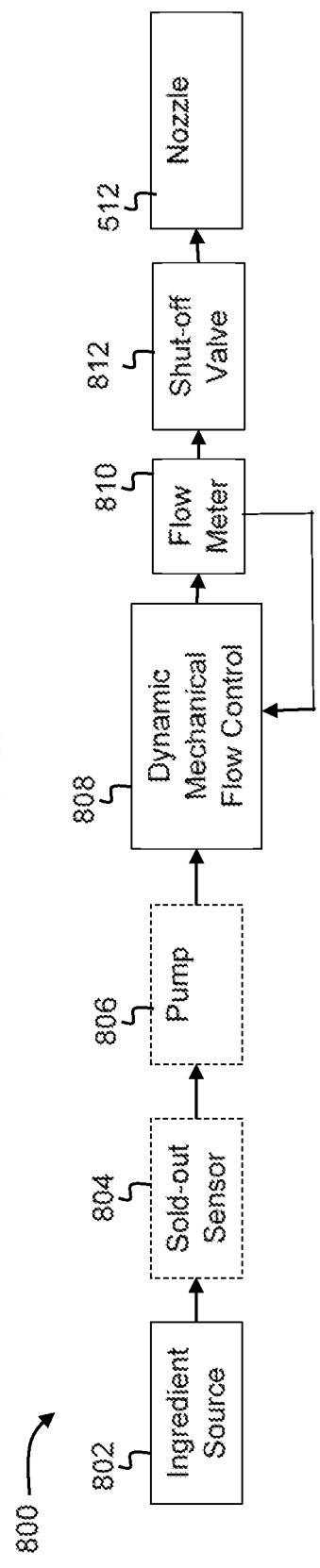
FIG. 8 illustrates an exemplary fluidic circuit with a dynamic mechanical flow control and flow meter suitable for implementing the several embodiments of the disclosure.

FIGS. 6-8 illustrate exemplary fluidic circuits 600-800 with pumping or metering devices from ingredient sources 602, 702, 802 to the nozzle 512 of the beverage dispenser 504. The beverage dispenser 504 may include none, one, or a plurality of the fluidic circuits shown in FIGS. 6-8. For each ingredient source, the beverage dispenser 504 may include one of the fluidic circuits shown in FIGS. 6-8. For example, each of the pumping or metering devices 108, 110, 112 may be implemented as one of the fluidic circuits shown in FIGS. 6-8.

FIG. 6 illustrates an exemplary fluidic circuit 600 with a positive displacement pump 610 suitable for implementing the several embodiments of the disclosure. The fluidic circuit 600 provides a fluid path from the ingredient source 602 to the nozzle 512. The ingredient source 602 may be a micro-ingredient source or a macro-ingredient source housed in the ingredient matrix 524 of the beverage dispenser 504, remote from the beverage dispenser 504 in the front room (e.g., adjacent to the beverage dispenser 504 or under a counter on which the beverage dispenser 504 is located), or located in the back room. The positive displacement pump 610 may meter a predetermined volume or flow rate of ingredient from the ingredient source 602 to the nozzle 512. The positive displacement pump 610 may be a piston pump, controlled gear pump, peristaltic pump, nutating pump, diaphragm pump, or other such positive displacement pump for metering a fixed volume of flow rate of a fluid with each cycle of the pump.

The fluidic circuit 600 may optionally include a sold-out sensor 604 for detecting when the ingredient source 602 is empty. When the ingredient source 602 is remotely located from the beverage dispenser 504, the fluidic circuit 600 may also optionally include an auxiliary pump 606 for providing a pressurized supply of the beverage ingredient to the beverage dispenser 504. Within or immediately adjacent to the beverage dispenser 504, the fluidic circuit 600 may include a pressure regulator 608 such that the inlet of the positive displacement pump 610 receives a lower or zero pressure supply of beverage ingredient. The fluidic circuit 600 may also optionally include a shut-off valve 612 that is configured to remain closed when an ingredient is not being dispensed so as to prevent beverage ingredient from dripping from the nozzle 512.

FIG. 7 illustrates an exemplary fluidic circuit 700 with a static mechanical flow control 708 suitable for implementing the several embodiments of the disclosure. The static mechanical flow control 708 receives a pressurized beverage ingredient from an ingredient source 702 and provides a fixed flow rate of the beverage ingredient to the nozzle 512. The static mechanical flow control 708 may be calibrated with a set screw for configuring the flow rate of the static mechanical flow control 708. A shut-off valve 710 downstream of the static mechanical flow control 708 may be actuated to open and close in order to dispense or prevent dispensing the beverage ingredient from the nozzle 512.

The ingredient source 702 may be a micro-ingredient source or a macro-ingredient source housed in the ingredient matrix 524 of the beverage dispenser 504, remote from the beverage dispenser 504 in the front room (e.g., adjacent to the beverage dispenser 504 or under a counter on which the beverage dispenser 504 is located), or located in the back room. The ingredient source 702 may also be the municipal water supply 536 or other pressurized ingredient source. When the ingredient source 702 is not pressurized, the fluidic circuit 700 may include a pump 706 for pressurizing the beverage ingredient from the ingredient source 702. The pump 706 may be any pump suitable for pressurizing the beverage ingredient from the ingredient source 702, such as a BIB pump, $CO_2$ driven pump, controlled gear pump, or positive displacement pump. The fluidic circuit 700 may also optionally include a sold-out sensor 704 for detecting when the ingredient source 702 is empty.

FIG. 8 illustrates an exemplary fluidic circuit 800 with a dynamic mechanical flow control 808, a flow meter 810, and a shut-off valve 812 suitable for implementing the several embodiments of the disclosure. The dynamic mechanical flow control 808 receives a pressurized beverage ingredient from an ingredient source 802 and provides an adjustable flow rate of the beverage ingredient to the nozzle 512. The dynamic mechanical flow control 808 may include a variable sized orifice that adjusts to dynamically change the flow rate of the beverage ingredient supplied to the nozzle 512 based on control signals provided by the one or more controllers 520. A flow meter 810 downstream of the dynamic mechanical flow control 808 measures a flow rate of the beverage ingredient being supplied by the dynamic mechanical flow control 808 and provides a feedback loop to the dynamic mechanical flow control 808 for controlling the variable sized orifice. A shut-off valve 812 downstream of the dynamic mechanical flow control 808 may be actuated to open and close in order to dispense or prevent dispensing the beverage ingredient from the nozzle 512.

The ingredient source 802 may be a micro-ingredient source or a macro-ingredient source housed in the ingredient matrix 524 of the beverage dispenser 504, remote from the beverage dispenser 504 in the front room (e.g., adjacent to the beverage dispenser 504 or under a counter on which the beverage dispenser 504 is located), or located in the back room. The ingredient source 802 may also be the municipal water supply 536 or other pressurized ingredient source. When the ingredient source 802 is not pressurized, the fluidic circuit 800 may include a pump 806 for pressurizing the beverage ingredient from the ingredient source 802. The pump 806 may be any pump suitable for pressurizing the beverage ingredient from the ingredient source 802, such as a BIB pump, $CO_2$ driven pump, controlled gear pump, or positive displacement pump. The fluidic circuit 800 may also optionally include a sold-out sensor 804 for detecting when the ingredient source 802 is empty.

While the components of the fluidic circuits 600-800 are shown in a particular order in FIGS. 6-8, any order of the components described above may be used. For example, the shut-off valve 812 may be upstream of the flow meter 810. Other variations are readily recognizable by those of ordinary skill in the art. Additionally, one or more heat exchangers (not shown) may be used at any location in the fluidic circuits of FIGS. 6-8. The heat exchanger may include an ice bin, water bath, cold plate, or remote recirculation system.

Figure 9:
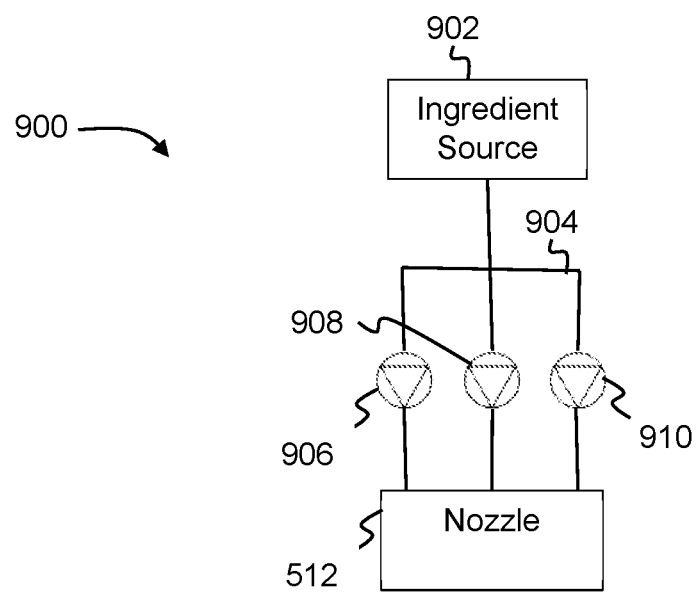
FIG. 9 illustrates an exemplary fluidic circuit with a plurality of independently controlled paths from a single ingredient source suitable for implementing the several embodiments of the disclosure.

FIG. 9 illustrates an exemplary fluidic circuit 900 with a plurality of independently controlled paths from a single ingredient source 902 to the nozzle 512 suitable for implementing the several embodiments of the disclosure. The fluidic circuit 900 includes a manifold 904 for supplying beverage ingredient to each of the independently controlled paths. Each path includes a pumping or metering device 906, 908, 910 for supplying beverage ingredient from the ingredient source 902 to the nozzle 512. The pumping or metering devices 906, 908, 910 may be configured as any of the fluidic circuits 600-800 shown in FIGS. 6-8. By having multiple independent paths from the ingredient source 902 to the nozzle 512, a larger range of flow rates are possible than using any one of the pumping or metering devices 906, 908, 910. For example, for a first flow rate of beverage ingredient from the ingredient source, only one of the pumping or metering devices 906, 908, 910 may be activated. For a second flow rate of the beverage ingredient from the ingredient source, a plurality of the pumping or metering devices 906, 908, 910 may be activated.

Figure 10:
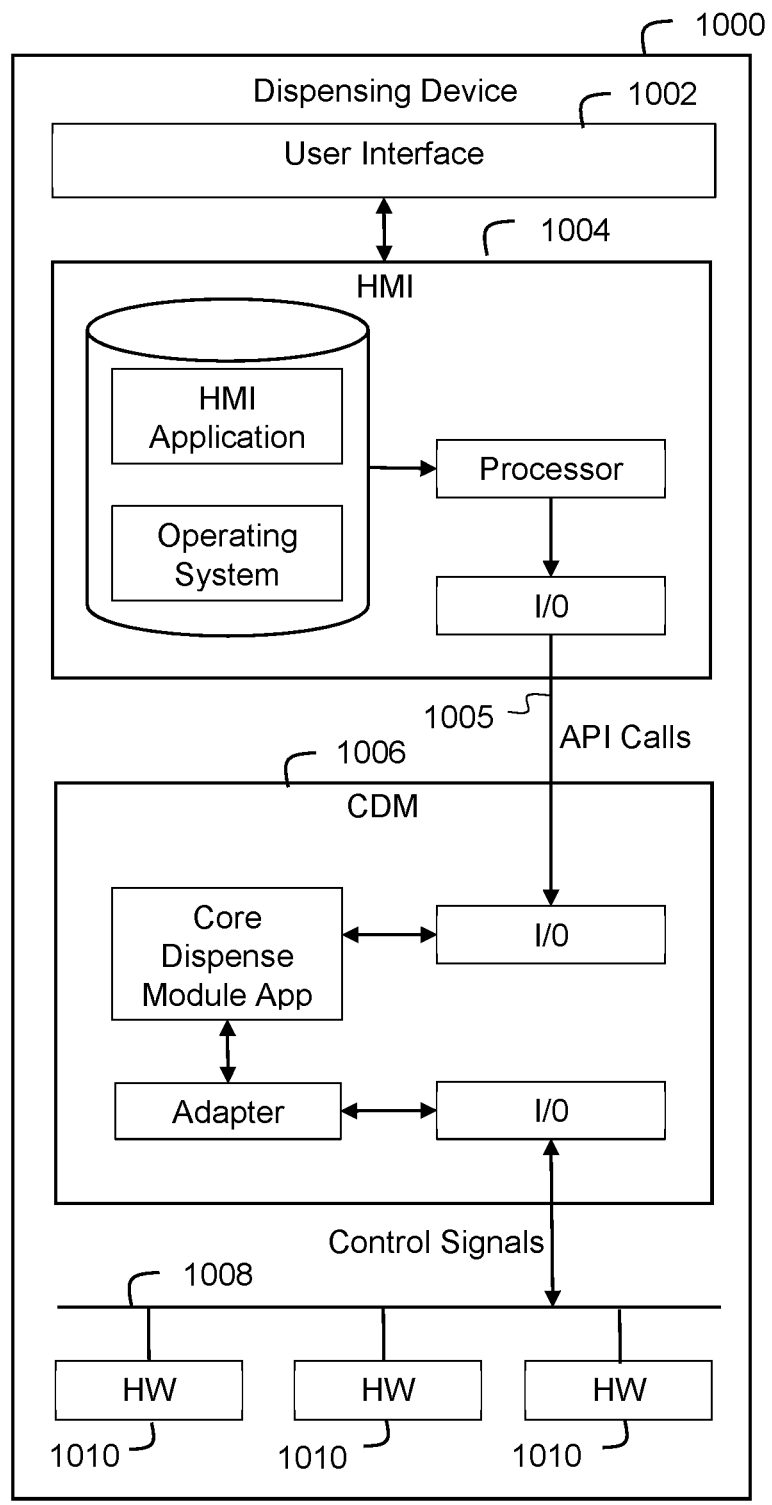
FIG. 10 illustrates an exemplary block diagram of a control architecture for a beverage dispenser suitable for implementing the several embodiments of the disclosure.

FIG. 10 illustrates an exemplary block diagram of a control architecture 1000 that may be used to control the beverage dispenser 504 suitable for implementing the several embodiments of the disclosure. As shown in FIG. 10, control architecture 1000 may comprise a core dispense module (CDM) 1006, a human machine interface (HMI) module 1004, a user interface (UI) 1002, and a machine bus (MBUS) 1005. HMI 1004 may connect to or otherwise interface and communicate with at least one external device (e.g., mobile device 552 or POS 554) being external to beverage dispenser 504. HMI 1004 may also control and update display screens on UI 1002. CDM 1006 may control flows from a plurality of pumps and/or valves 1010 in beverage dispenser 504 according to a recipe to mix and dispense a product (e.g., a beverage) from beverage dispenser 504.

Beverage ingredients (e.g., micro-ingredients, macro-ingredients, and/or diluents) may be combined to dispense various products that may include beverages or blended beverages (i.e., finished beverage products) from beverage dispenser 504. However, beverage dispenser 504 may also be configured to dispense beverage components individually.

An example of control architecture 1000 for beverage dispenser 504 may be described in U.S. Ser. No. 61/987,020, entitled "Dispenser Control Architecture", filed on May 1, 2014, the entirety of which is hereby incorporated by reference. MBUS 1005 may facilitate communication between HMI 1004 and CDM 1006 via one or more API calls. HMI 1004, MBUS 1005, and CDM 1006 may collectively comprise common core components, implemented as hardware or as combination of hardware and software, which may be adapted to provide customized functionality in beverage dispenser 504. Beverage dispenser 504 may further include memory storage and a processor. Examples of UI 1002 may be described in U.S. Ser. No. 61/877,549, entitled "Product Categorization User Interface for a Dispensing Device", filed on Sep. 13, 2013, the entirety of which is hereby incorporated by reference.

UI 1002 may detect what area of a touch screen has been touched by a user (e.g., user 108). In response, UI 1002 may send HMI 1004 data regarding where the touch screen was touched. In response, HMI 1004 may interpret this received data to determine whether to have UI 1002 display a different UI screen or to issue a command to CDM 1006. For example, HMI 1004 may determine that the user touched a portion of the touch screen corresponding to a beverage brand. In response, HMI 1004 may issue a command to CDM 1006 to pour the corresponding beverage brand. In response to receiving the command to pour the corresponding beverage brand, the CDM 1006 in turn issues commands via one or more control buses 1008 to the pumping or metering devices 1010 for the beverage ingredients needed to dispense the beverage brand. Or HMI 1004 may determine that the user touched a portion of the touch screen corresponding to a request for another screen. In response, HMI 1004 may cause UI 1002 to display the requested screen.

In some embodiments, UI 1002 in beverage dispenser 504 may be utilized to select and individually dispense one or more beverages. The beverages may be dispensed as beverage components in a continuous pour operation whereby one or more selected beverage components continue to be dispensed while a pour input is actuated by a user or in a batch pour operation where a predetermined volume of one or more selected beverage components are dispensed (e.g., one ounce at a time). UI 1002 may be addressed via a number of methods to select and dispense beverages. For example, a user may interact with UI 1002 via touch input to navigate one or more menus from which to select and dispense a beverage. As another example, a user may type in a code using an onscreen or physical keyboard (not shown) on beverage dispenser 504 to navigate one or more menus from which to select and dispense a beverage. As a further example, a user may interact with the HMI 1004 via a user interface of an application on the mobile device 552.

UI 1002, which may include a touch screen and a touch screen controller, may be configured to receive various commands from a user (i.e., consumer input) in the form of touch input, generate a graphics output and/or execute one or more operations with beverage dispenser 504 (e.g., via HMI 1004 and/or CDM 1006), in response to receiving the aforementioned commands. A touch screen driver in HMI 1004 may be configured to receive the consumer or customer inputs and generate events (e.g., touch screen events) that may then be communicated through a controller to an operating system of HMI 1004.

Beverage dispenser 504 may be in communication with one or more external device (e.g., mobile device 552 or POS 554). In some embodiments, the communication between beverage dispenser 504 and the external device may be accomplished utilizing any number of communication techniques including, but not limited to, near-field wireless technology such as BLUETOOTH, Wi-Fi and other wireless or wireline communication standards or technologies, via a communication interface.

Figure 11:
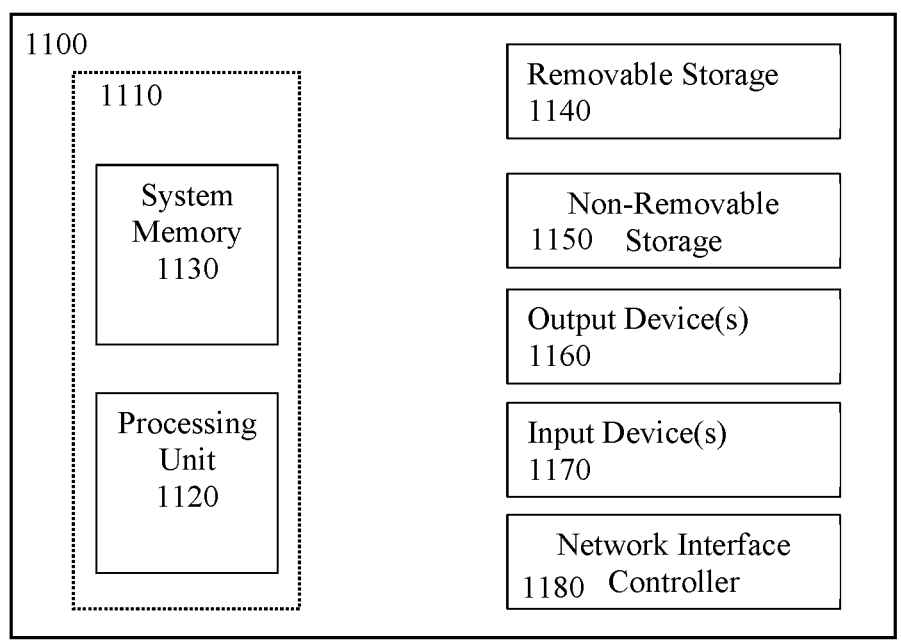
FIG. 11 illustrates an exemplary computer system suitable for implementing the several embodiments of the disclosure.

FIG. 11 illustrates an exemplary computer system 1100 suitable for implementing the several embodiments of the disclosure. For example, one or more components or controller components of the beverage dispenser 504 may be implemented as the computer system 1100. In some implementations, one or both of the HMI 1004 and the CDM 1006 may be implemented as the computer system 1100.

It should be appreciated that the logical operations described herein with respect to the various figures may be implemented (1) as a sequence of computer implemented acts or program modules (i.e., software) running on a computing device (e.g., the computing device described in FIG. 11), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts, and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 11, an example computing device 1100 upon which embodiments of the invention may be implemented is illustrated. For example, each of the content source, key server, segmentations servers, caching servers, and client devices described herein may each be implemented as a computing device, such as computing device 1100. It should be understood that the example computing device 1100 is only one example of a suitable computing environment upon which embodiments of the invention may be implemented. Optionally, the computing device 1100 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In some embodiments, the computing device 1100 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In some embodiments, virtualization software may be employed by the computing device 1100 to provide the functionality of a number of servers that is not directly bound to the number of computers in the computing device 1100. For example, virtualization software may provide twenty virtual servers on four physical computers. In some embodiments, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third-party provider. Some cloud computing environments may comprise cloud computing resources owned and operated by the enterprise as well as cloud computing resources hired and/or leased from a third-party provider.

In its most basic configuration, computing device 1100 typically includes at least one processing unit 1106 and system memory 1104. Depending on the exact configuration and type of computing device, system memory 1104 may be volatile (such as random-access memory (RAM)), non-volatile (such as read-only memory (ROM), flash memory, etc.), or some combination of the two. This most basic configuration is illustrated in FIG. 11 by dashed line 1102. The processing unit 1106 may be a standard programmable processor that performs arithmetic and logic operations necessary for operation of the computing device 1100. While only one processing unit 1106 is shown, multiple processors may be present. Thus, while instructions may be discussed as executed by a processor, the instructions may be executed simultaneously, serially, or otherwise executed by one or multiple processors. The computing device 1100 may also include a bus or other communication mechanism for communicating information among various components of the computing device 1100.

Computing device 1100 may have additional features/functionality. For example, computing device 1100 may include additional storage such as removable storage 1108 and non-removable storage 1110 including, but not limited to, magnetic or optical disks or tapes. Computing device 1100 may also contain network connection(s) 1116 that allow the device to communicate with other devices such as over the communication pathways described herein. The network connection(s) 1116 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 1100 may also have input device(s) 1114 such as a keyboard, keypads, switches, dials, mice, track balls, touch screens, voice recognizers, card readers, paper tape readers, or other well-known input devices. Output device(s) 1112 such as a printer, video monitors, liquid crystal displays (LCDs), touch screen displays, displays, speakers, etc. may also be included. The additional devices may be connected to the bus in order to facilitate communication of data among the components of the computing device 1100. All these devices are well known in the art and need not be discussed at length here.

The processing unit 1106 may be configured to execute program code encoded in tangible, computer-readable media. Tangible, computer-readable media refers to any media that is capable of providing data that causes the computing device 1100 (i.e., a machine) to operate in a particular fashion. Various computer-readable media may be utilized to provide instructions to the processing unit 1106 for execution. Example tangible, computer-readable media may include, but is not limited to, volatile media, non-volatile media, removable media, and non-removable media implemented in any method or technology for storage of information such as computer readable instructions, data structures, program modules or other data. System memory 1104, removable storage 1108, and non-removable storage 1110 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable programmable read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 1106 may execute program code stored in the system memory 1104. For example, the bus may carry data to the system memory 1104, from which the processing unit 1106 receives and executes instructions. The data received by the system memory 1104 may optionally be stored on the removable storage 1108 or the non-removable storage 1110 before or after execution by the processing unit 1106.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A beverage dispenser, comprising:
   a nozzle configured to dispense a plurality of beverage ingredients to produce a finished beverage;
   a user interface configured to receive a selection of a beverage to be dispensed and a selection of a nutritive level for the beverage, wherein the nutritive level selection is one of a plurality of preconfigured nutritive levels, where each of the nutritive levels has a calorie range that is different than the other nutritive levels;
   a plurality of pumping or metering devices, each configured to supply a beverage ingredient from an ingredient source to the nozzle;
   a controller configured to look up a nutritive level recipe based on the nutritive level selection and the beverage selection, the nutritive level recipe comprising a preconfigured amount of one or more sweeteners to be dispensed to produce the beverage within the calorie range of the selected nutritive level based on a flavor profile of the selected beverage,
   wherein the controller is further configured to activate one or more of the plurality of pumping or metering devices based on the nutritive level recipe to dispense the amount of the one or more sweeteners,
   wherein the nutritive level recipe for the selected nutritive level is based on the selected beverage such that, for a given nutritive level selected, the beverage dispenser is configured to dispense different preconfigured combinations of sweeteners and/or different preconfigured ratios of sweeteners for different selected beverages.

2. The beverage dispenser of claim 1, wherein the nutritive level recipe comprises an amount of a plurality of sweeteners to be dispensed to produce the beverage at the selected nutritive level.

3. The beverage dispenser of claim 1, wherein the pumping or metering devices include one or more of a positive displacement pump, a static mechanical control valve, and a dynamic mechanical control valve.

4. The beverage dispenser of claim 1, wherein the controller is further configured to look up a beverage recipe for the beverage, the beverage recipe comprises amounts of a plurality of ingredients other than the one or more sweeteners to be dispensed to produce the beverage.

5. The beverage dispenser of claim 4, wherein the nutritive level recipe and the beverage recipe are maintained in a combined recipe.

6. The beverage dispenser of claim 4, wherein the plurality of ingredients comprise one or more non-sweetener micro-ingredients, macro-ingredients, and/or diluents.

7. The beverage dispenser of claim 1, wherein the nutritive level recipe is maintained in a table of a plurality of recipes, each of the plurality of recipes comprises an amount of one or more sweeteners to be dispensed to produce the beverage at different nutritive level.

8. The beverage dispenser of claim 7, wherein one or more of the plurality of recipes comprises a different combination of one or more sweeteners than the nutritive level recipe.

9. The beverage dispenser of claim 1, wherein the one or more sweeteners comprise a plurality of sweeteners including one or more caloric sweeteners and one or more non-caloric sweeteners.

10. The beverage dispenser of claim 1, wherein the user interface is further configured to receive a selection of a second beverage to be dispensed at the nutritive level, wherein a second nutritive level recipe comprises a second amount of one or more sweeteners to be dispensed to produce the second beverage at the selected nutritive level.

11. A method of dispensing a beverage from a beverage dispenser, comprising:
   receiving, at a user interface of the beverage dispenser, a selection of the beverage to be dispensed and a selection of a nutritive level for the beverage, wherein the nutritive level selection is one of a plurality of preconfigured nutritive levels, where each of the nutritive levels has a calorie range that is different than the other nutritive levels;
   looking up a nutritive level recipe based on the nutritive level selection and the beverage selection, the nutritive level recipe comprising a preconfigured amount of one or more sweeteners to be dispensed to produce the beverage within the calorie range of the selected nutritive level based on a flavor profile of the selected beverage, wherein the nutritive level recipe for the selected nutritive level is based on the selected beverage such that, for a given nutritive level selected, the beverage dispenser dispenses different preconfigured combinations of sweeteners and/or different preconfigured ratios of sweeteners for different selected beverages;
   activating one or more of a plurality of pumping or metering devices on the beverage dispenser based on the nutritive level recipe to dispense the amount of the one or more sweeteners via a nozzle.

12. The method of claim 11, wherein the nutritive level recipe comprises an amount of a plurality of sweeteners to be dispensed to produce the beverage at the selected nutritive level.

13. The method of claim 11, wherein the pumping or metering devices include one or more of a positive displacement pump, a static mechanical control valve, and a dynamic mechanical control valve.

14. The method of claim 11, further comprising:
   looking up a beverage recipe for the beverage, the beverage recipe comprises amounts of a plurality of ingredients other than the one or more sweeteners to be dispensed to produce the beverage.

15. The method of claim 14, wherein the nutritive level recipe and the beverage recipe are maintained in a combined recipe.

16. The method of claim 14, wherein the plurality of ingredients comprise one or more non-sweetener micro-ingredients, macro-ingredients, and/or diluents.

17. The method of claim 11, wherein the nutritive level recipe is maintained in a table of a plurality of recipes, each of the plurality of recipes comprises an amount of one or more sweeteners to be dispensed to produce the beverage at different nutritive level.

18. The method of claim 17, wherein one or more of the plurality of recipes comprises a different combination of one or more sweeteners than the nutritive level recipe.

19. The method of claim 11, wherein the one or more sweeteners comprise a plurality of sweeteners including one or more caloric sweeteners and one or more non-caloric sweeteners.

20. The method of claim 11, further comprising:
   receiving, at a user interface of the beverage dispenser, a selection of a second beverage to be dispensed at the nutritive level, wherein a second nutritive level recipe comprises a second amount of one or more sweeteners to be dispensed to produce the second beverage at the selected nutritive level.

\* \* \* \* \*